(12) United States Patent
Zhao-Wilson

(10) Patent No.: US 8,436,224 B2
(45) Date of Patent: May 7, 2013

(54) METHODS FOR TESTING FOR CALORIC RESTRICTION (CR) MIMETICS

(75) Inventor: Xi Zhao-Wilson, Los Gatos, CA (US)

(73) Assignee: BioMarker Pharmaceuticals, Inc., San Jose, CA (US)

( * ) Notice: Subject to any disclaimer, the term of this patent is extended or adjusted under 35 U.S.C. 154(b) by 0 days.

(21) Appl. No.: 13/154,035

(22) Filed: Jun. 6, 2011

(65) Prior Publication Data

US 2012/0030777 A1     Feb. 2, 2012

Related U.S. Application Data

(62) Division of application No. 11/377,986, filed on Mar. 17, 2006, now Pat. No. 7,960,605.

(51) Int. Cl.
    *G01N 33/483*      (2006.01)
    *C12Q 1/02*      (2006.01)

(52) U.S. Cl.
    USPC ............................... 800/3; 435/29

(58) Field of Classification Search .................. None
See application file for complete search history.

(56) References Cited

U.S. PATENT DOCUMENTS

| | | | |
|---|---|---|---|
| 6,406,853 B1 | 6/2002 | Spindler | |
| 6,470,894 B2 | 10/2002 | Hersh et al. | |
| 6,569,624 B1 | 5/2003 | Weindruch et al. | |
| 6,638,545 B1 | 10/2003 | Rombi | |
| 2003/0124540 A1 | 7/2003 | Spindler | |
| 2003/0224360 A9 | 12/2003 | Spindler | |
| 2004/0047896 A1 | 3/2004 | Malnoe et al. | |
| 2004/0180003 A1 | 9/2004 | Spindler et al. | |
| 2004/0191775 A1 | 9/2004 | Spindler et al. | |
| 2005/0013776 A1 | 1/2005 | Spindler et al. | |
| 2005/0100617 A1 | 5/2005 | Malnoe et al. | |
| 2005/0266438 A1 | 12/2005 | Spindler et al. | |
| 2006/0276393 A1* | 12/2006 | Milburn et al. .............. | 514/12 |

OTHER PUBLICATIONS

Lee et al. (Life Sciences 2003; 73: 167-179).*
Noda et al. (IUBMB Life, Jun. 1997; 42(1): 35-44).*
Beauseigneur et al. (Biochem J. 1996; 320(2): 571-576).*
Interpharma-Praha, (2001), 3 pages.
Bastianetto, S., et al., "Natural Antioxidants and Neurodegenerative Diseases", Frontiers in Bioscience 9, (Sep. 1, 2004), pp. 3447-3452.
Horstink, M., et al., "No male predominance in a-synuclein Parkinson's disease but the affected female fetus might be less viable", J Neurol Neurosurg Psychiatry 72, (2002), pp. 274-280.
Ingram, et al., Aging Cell, 5, (2006), pp. 97-108.
Kamat, Jayashree P., et al., "Antioxidant properties of *Asparagus racemosus* against damage induced by y-radiation in rat liver mitochondria", Journal of Ethnopharmacology 71, (2000), pp. 425-435.
Lee, Si E., et al., "Screening of medicinal plant extracts for antioxidant activity", Life Sciences 73, (2003), pp. 167-179.
Liu, Jiankang, et al., "Age-associated mitochondrial oxidative decay: Improvement of carnitine acetyltransferase substrate-binding affinity and activity in brain by feeding old rats acetyl-L-carnitine and/or R-a-lipoic acid", PNAS, Vo. 99, No. 4, (Feb. 19, 2002), pp. 1876-1881.
Marsh, J. Lawrence, et al., "Fly models of Huntington's disease", Human Molecular Genetics, vol. 12, Review Issue 2, (2003), R187-R193.
Mattson, Mark P., et al., "Suppression of brain aging and neurodegenerative disorders by dietary restriction and environmental enrichments: molecular mechanisms". Mechanisms of Ageing and Development 122, (2001), pp. 757-778.
Mercer, Linda D., et al., "Dietary polyphenols protect dopamine neurons from oxidative insults and apoptosis: investigations in primary rat mesencephalic cultures", Biochemical Pharmacology 69, (2005), pp. 339-345.
Noda, Yasuko, et al., "Hydroxyl and Superoxide Anion Radical Scavenging Activities of Natural Source Antioxidants Using the Computerized JES-FR30 ESR Spectrometer System", Biochemsitry and Molecular Biology International, vol. 42, No. 1, (Jun. 1997), pp. 35-44.
Parker, J. A., et al., "Resveratrol rescues mutant polyglutamine cytotoxicity in nematode and mammalian neurons", Nature Genetics, vol. 37, No. 4, (Apr. 2005), pp. 349, 350 & 355.
Pendleton, Robert G., et al., "Effects of Pharmacological Agents upon a Transgenic Model of Parkinson's Disease in *Drosophila nnelanogaster*", The Journal of Pharmacology and Experimental Therapeutics, vol. 300, No. 1, (2002), pp. 91-96.
Van Raamsdonk, Jeremy M., et al., "Experimental models of Huntington's disease", Drug Discovery Today: Disease Models, vol. 2, No. 4, (2005), pp. 291-297.
Weindruch, Richard, et al., "Caloric Restriction Minnetics: Metabolic Interventions", Journals of Gerontology. vol. 56A (Special Issue I), (2001), pp. 20-33.
Wood, Jason G., et al., "Sirtuin activators mimic caloric restriction and delay ageing in metazoans", Nature, vol. 430, No. 5, (Aug. 2004), pp. 686-689 & 107.
Marsh, J. Lawrence, et al., "Fly models of Huntington's disease," Human Molecular Genetics, 2003, pp. R187-R193, 12(2).
Gruber, J., et al., "Evidence for a Trade-off Between Survival and Fitness Caused by Resveratrol Treatment of *Caenorhabditis elegans*," Ann N. Y. Acad, Sci., Apr. 2007, pp. 530-542, 1100. (Abstract).
Loren, Karl, "What is OPC Grape Seed Extract and How Does it Work?" http://www.oralchelation.com/ingred/grapeseedextract.htm, Dec. 21, 2006.
Agrawal, Namita, et al., "Identification of Combinatorial Drug Regimens for Treatment of Huntington's Disease Using *Drosophila*," PNAS, 2005, pp. 3777-3781, 102(10).

(Continued)

*Primary Examiner* — Scott Long
(74) *Attorney, Agent, or Firm* — Blakely Sokoloff Taylor & Zafman LLP

(57) ABSTRACT

Methods for treating neurological diseases and for testing Caloric Restriction (CR) mimetics or CR mimetic candidates. In one exemplary method, a CR mimetic candidate is administered to a transgenic animal and the effects of the administering are determined; the transgenic animal includes an added gene from another type of animal or a modified gene which is designed to produce a disease or ailment of another type of animal, and the method seeks to determine whether the CR mimetic candidate improves the disease or ailment. Methods relating to neurological disease and other methods relating to CR mimetic testing are also described.

15 Claims, 15 Drawing Sheets

OTHER PUBLICATIONS

Agrawal, Namita, et al., "Identification of Combinatorial Drug Regimens for Treatment of Huntington's Disease Using *Drosophila*," HDAC, http://www.hdac.org/features/article.php?p_articleNumber=132, Feb. 16, 2005.

King, M.T., et al., "Mutagenicity Studies with X-Ray-Contrast Media, Analgesics, Antipyretics, Antirheumatics and Some Other Pharmaceutical Drugs in Bacterial, *Drosophila* and Mammalian Test Systems," Mutat. Res., Jan. 1979, pp. 33-43, 66(1). (Abstract).

Wolfgang, William J., et al., "Suppression of Huntington's Disease Pathology in *Drosophila* by Human Single-Chain Fv Antibodies," PNAS, Aug. 9, 2005, pp. 11563-11568, 102(32).

Haberman, Allan B., "Therapeutic Strategies in Animal Models: The Case of Alzheimer's Disease," Genetic Engieering News, Sep. 15, 2004, pp. 28 & 31, 24(16).

Ingram, D.K., "Development of Calorie Restriction Mimetics as a Prolongevity Strategy," Ann N.Y. Acad. Sci., Jun. 2004, pp. 412-423, 1019. (Abstract).

De Cabo, Rafael, "Laboratory of Experimental Gerontology," http://www.grc.nia.nih.gov/branches/irp/rdecabo.htm, Mar. 12, 2007.

Baur, J.A., et al., "Resveratrol Improves Health and Survival of Mice on a High-Calorie Diet," Nature, Nov. 16, 2006, pp. 337-342, 444(7117). (Abstract).

Anisimov, V.N., "Effect of Metformin on Life Span and on the Development of Spontaneous Mammary Tumors in HER-2/neu Transgenic Mice," Exp. Gerontol., Aug./Sep. 2005, pp. 685-693, 40(8-9). (Abstract).

Lamming, Dudley W., et al., "Small Molecules that Regulate Lifespan: Evidence for Xenohormesis," Molecular Microbiology, 2004, pp. 1003-1009, 53(4).

Hansen, Barbara Caleen, "Symposium: Calorie Restriction: Effects on Body Compsition, Insulin Signaling and Aging," The Journal of Nutrition, 2001, pp. 900S-902S.

Feany, et al., (Climbing assay), Harvard University, *Nature*, Mar. 23, 2000, 404 (6776):394-8.

Kanno, T.,et al., "Dysfunction of Mouse Liver Mitochondria Induced by 2,2'-azobis-(2-amidinopropane) Dihydrochloride, a Radical Initiator, In Vitro and In Vivo," *Free Radical Res.*, Sep. 1994: 21(4) pp. 223-234. PMID: 7827694.

Krahenbuhl, S. et al. "Decreased activities of Ubiquinol: Ferricytochrome c oxidoredactase 9complex III) and ferrocytochrome c:oxygen oxidoreductase (complex IV) in liver mitochondria from rats with hydroxycobalamin [c-lactam]—induced methylmalonic aciduria." *J Biol Chem.* Nov. 5, 1991; 266(31):20998-1003.

Liu J., et al. Antioxidant and Free radical scavenging activities of Gastrodia elate B1. and *Uncaria rhynchophylla* (Miq.) Jacks. *Neuropharmacology.* Dec. 1992; 31 (12): 1287-98. PMID: 1470304.

Liu, et al., "Antioxidant and por—oxidant assay for a new drug GEPC: detected by ESR spectrometry and by protective effects on lipid peroxidation and biomolecule degradation." *Res Commun Chem Pathol Paharmacol.* Nov. 1993; 92(2): 151-66. PMID: 8303085.

Liu, et al., "Antioxidant and pro-oxidant activities of p-hydroxybenzyl alcohol and vanillin: effects on free radical, brain peroxidation and degradation of benzoate, deoxyribose, amino acids and DNA." *Neuropharmacology.* Jul. 1993: 32(7):659-69, PMID: 7689708.

Pendleton R.G., et al., "Effects of Pharmacological Agents Upon a Transgenic Mode of Parkinson's Disease in *Drosophila melanogaster*" (Climbing assay), *J Pharmacol Exp Ther*. Jan. 2002: 300 (1):9106. Erratum in J. Pharmacol Exp Ter Mar. 2002: 300(3):1131. PMID 11752102.

Picklo, M.J., et al., in "Acrolein inhibits respiration in isolation brain mitochondria," *Biochem. Biophys. Acta* Feb. 14, 2001, 1535(2), pp. 145-152. PMID: 11342003.

Weindruch, et al. "The Retardation of Aging and Disease by Dietary Restriction", C.C. Thomas, Springfield, IL, 1988, Charles C. Thomas Pub Ltd (Dec. 1988), ISBN: 0398057967.

* cited by examiner

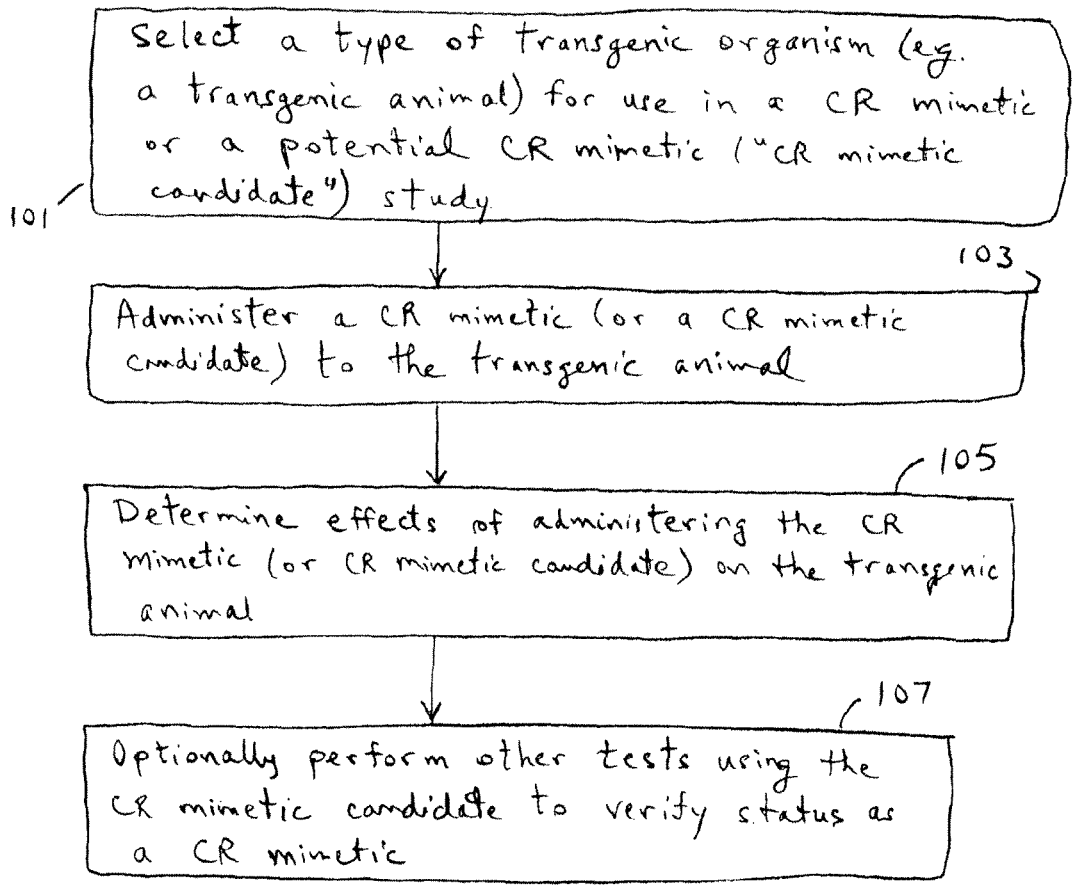

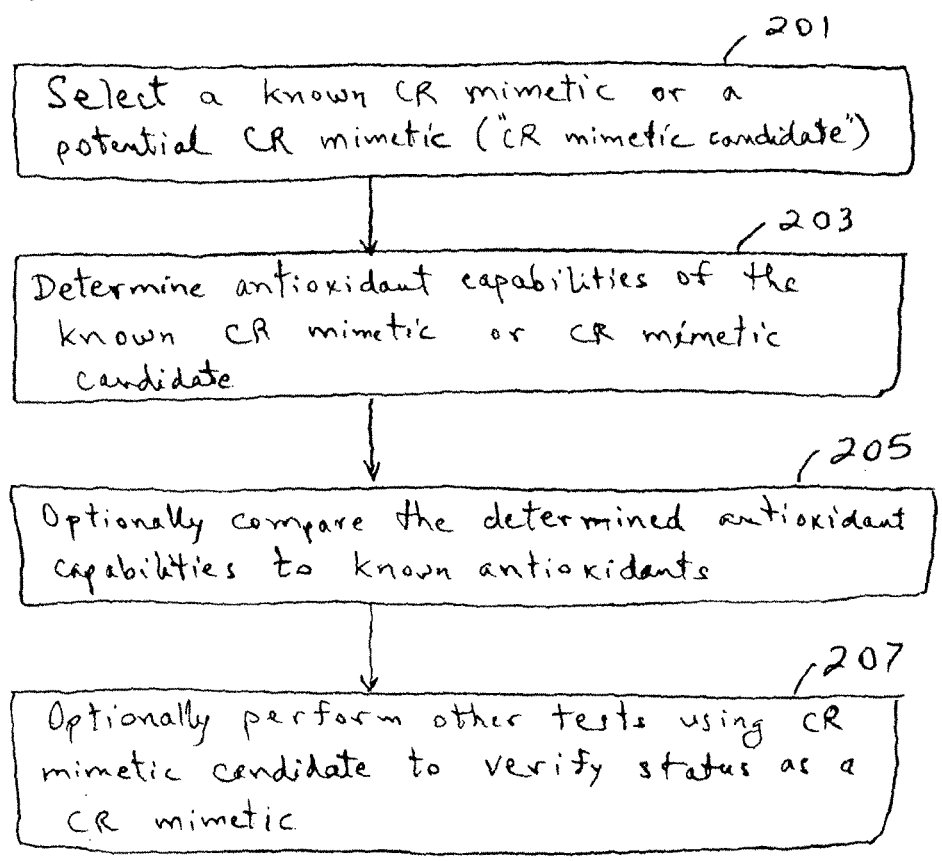

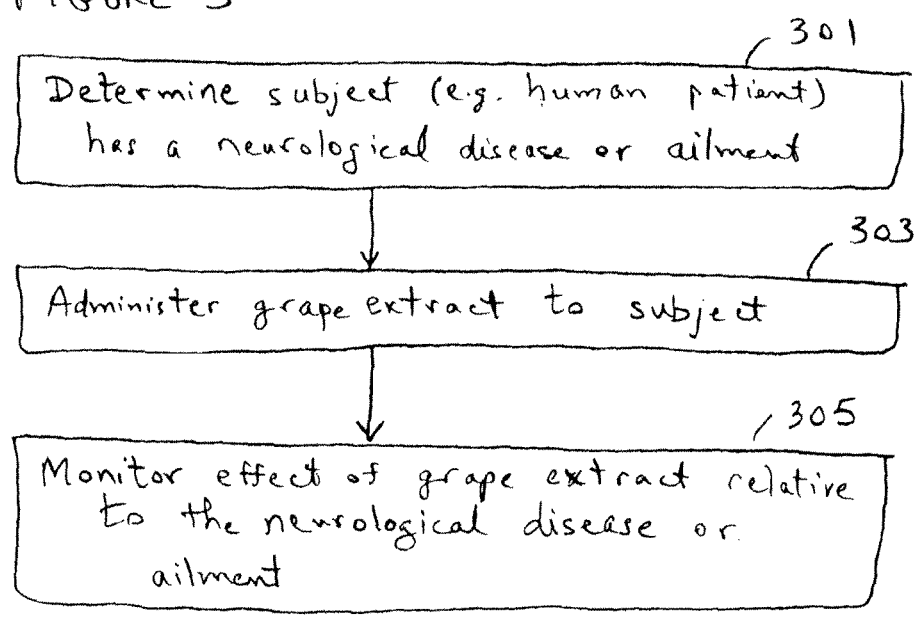

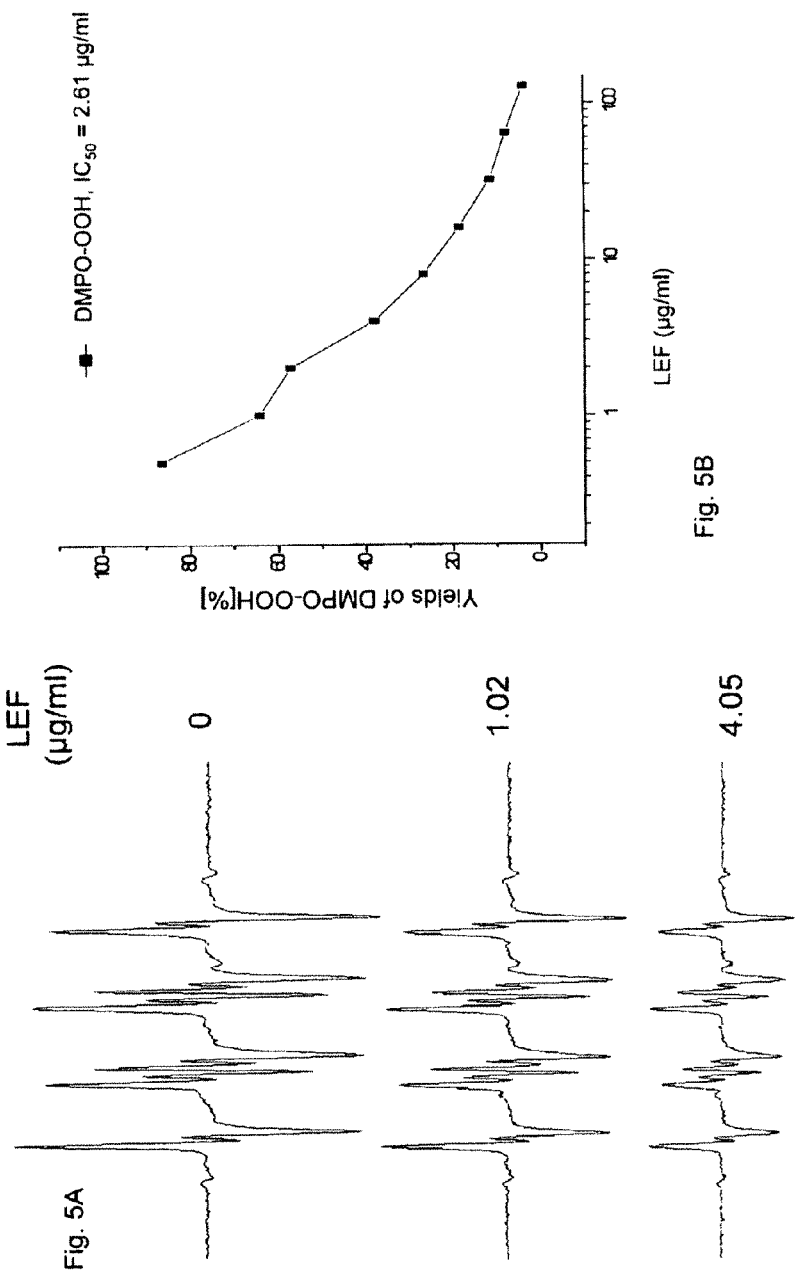

Fig. 7 Comparison of the 50% free radical scavenging with some well known scavengers (mg/ml)

| Radicals | ALC | LA | EPCK1 | Resv | LEF | UTR | C-Med |
|---|---|---|---|---|---|---|---|
| Hydroxyl | >60 | 1.97 | 21.8 | | 24.6 | | |
| Superoxide | - | | | 1.7 | 0.0026 | | 0.0072 |
| Lipid | 2.24 | 1.32 | 2.33 | | 3.68 | 1.23 | 1.35 |

Fig. 10B

| | P value of PD male climbing assay | | | | | | | | |
|---|---|---|---|---|---|---|---|---|---|
| | T test (VS PD male) | | | | | | | one-way ANOVA | |
| age | LEF-0.08 | LEF-0.16 | LEF-0.31 | LEF-0.64 | LEF-1.25 | LEF-2.5 | | 6 groups | 5 groups |
| 3 | 0.4286 | 0.2184 | 0.2512 | 0.4835 | 0.443 | 0.3896 | | 0.9714 | 0.9128 |
| 6 | 0.2808 | 0.2777 | 0.4891 | 0.1381 | 0.3839 | 0.4695 | | 0.0046 | 0.6383 |
| 12 | 0.0156 | 0.2791 | 0.2006 | 0.1144 | 0.0293 | 0.1969 | | 0 | 0.0216 |
| 18 | 0.2103 | 0.0059 | 0.0217 | 0.0379 | 0.1255 | 0.0008 | | 0.0206 | 0.0671 |
| 24 | 0.0567 | 0.0102 | 0.0064 | 0.039 | 0.0256 | 0.0316 | | 0.0006 | 0.201 |
| 30 | 0.0303 | 0.0346 | 0.0003 | 0.0494 | 0.1543 | 0.073 | | 0.0062 | 0.2566 |
| 36 | 0.2041 | 0.0245 | 0.1974 | 0.0626 | 0.0582 | 0.48 | | 0.0004 | 0.7294 |
| 42 | 0.0978 | 0.0472 | 0.0574 | 0.1906 | 0.1631 | 0.0402 | | 0.0008 | 0.5086 |
| 48 | 0.0666 | 0.1347 | 0.0458 | 0.0298 | 0.0053 | 0.0413 | | 0.5135 | 0.5745 |

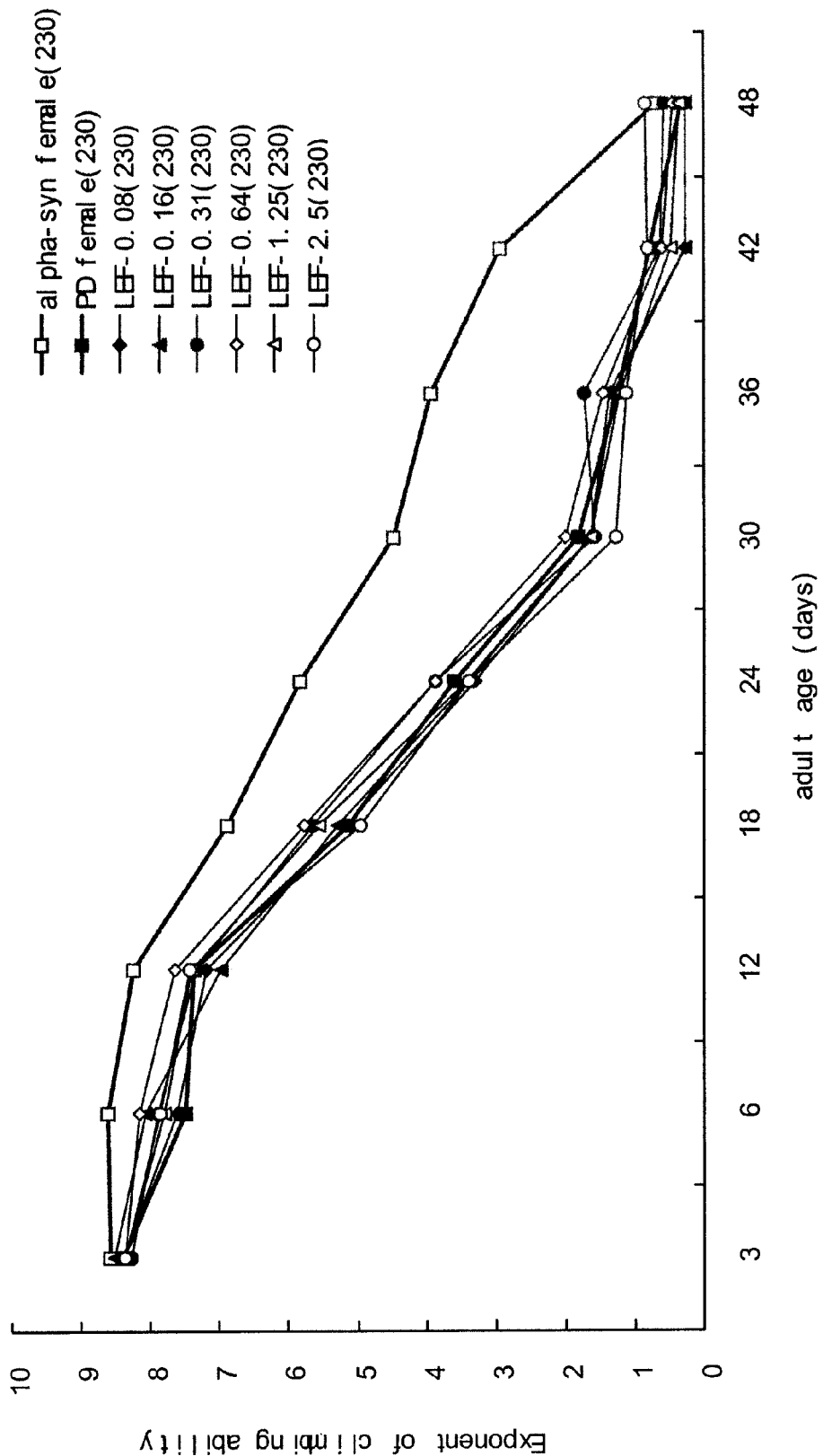

Fig. 11B

| | P value of PD female climbing assay | | | | | | | |
|---|---|---|---|---|---|---|---|---|
| | T test (VS PD female) | | | | | | one-way ANOVA | |
| age | LEF-0.08 | LEF-0.16 | LEF-0.31 | LEF-0.64 | LEF-1.25 | LEF-2.5 | 6 groups | 5 groups |
| 3 | 0.4777 | 0.2189029 | 0.2047994 | 0.4502953 | 0.460158418 | 0.4280845 | 0.6726292 | 0.89042 |
| 6 | 0.3039 | 0.0141646 | 0.0752244 | 0.0040035 | 0.09751197 | 0.0759187 | 0.0002366 | 0.0811098 |
| 12 | 0.1348 | 0.0721119 | 0.4650075 | 0.1400165 | 0.471994693 | 0.4922151 | 0.0003213 | 0.2063548 |
| 18 | 0.4576 | 0.4004244 | 0.1971219 | 0.1001888 | 0.175520192 | 0.266957 | 1.983E-05 | 0.3413329 |
| 24 | 0.27 | 0.3335063 | 0.3203221 | 0.3224043 | 0.388482115 | 0.3638943 | 1.737E-07 | 0.7259385 |
| 30 | 0.3972 | 0.2655646 | 0.2701781 | 0.3951157 | 0.257742219 | 0.0917148 | 6.816E-13 | 0.6116755 |
| 36 | 0.3639 | 0.384549 | 0.1463231 | 0.2590598 | 0.490512006 | 0.3528735 | 4.86E-10 | 0.8291839 |
| 42 | 0.0885 | 0.1031585 | 0.4160721 | 0.3965509 | 0.235126274 | 0.4588595 | 6.011E-08 | 0.758376 |
| 48 | 0.3893 | 0.4186182 | 0.0344782 | 0.1961887 | 0.312816881 | 0.0388197 | 0.0595696 | 0.0454762 |

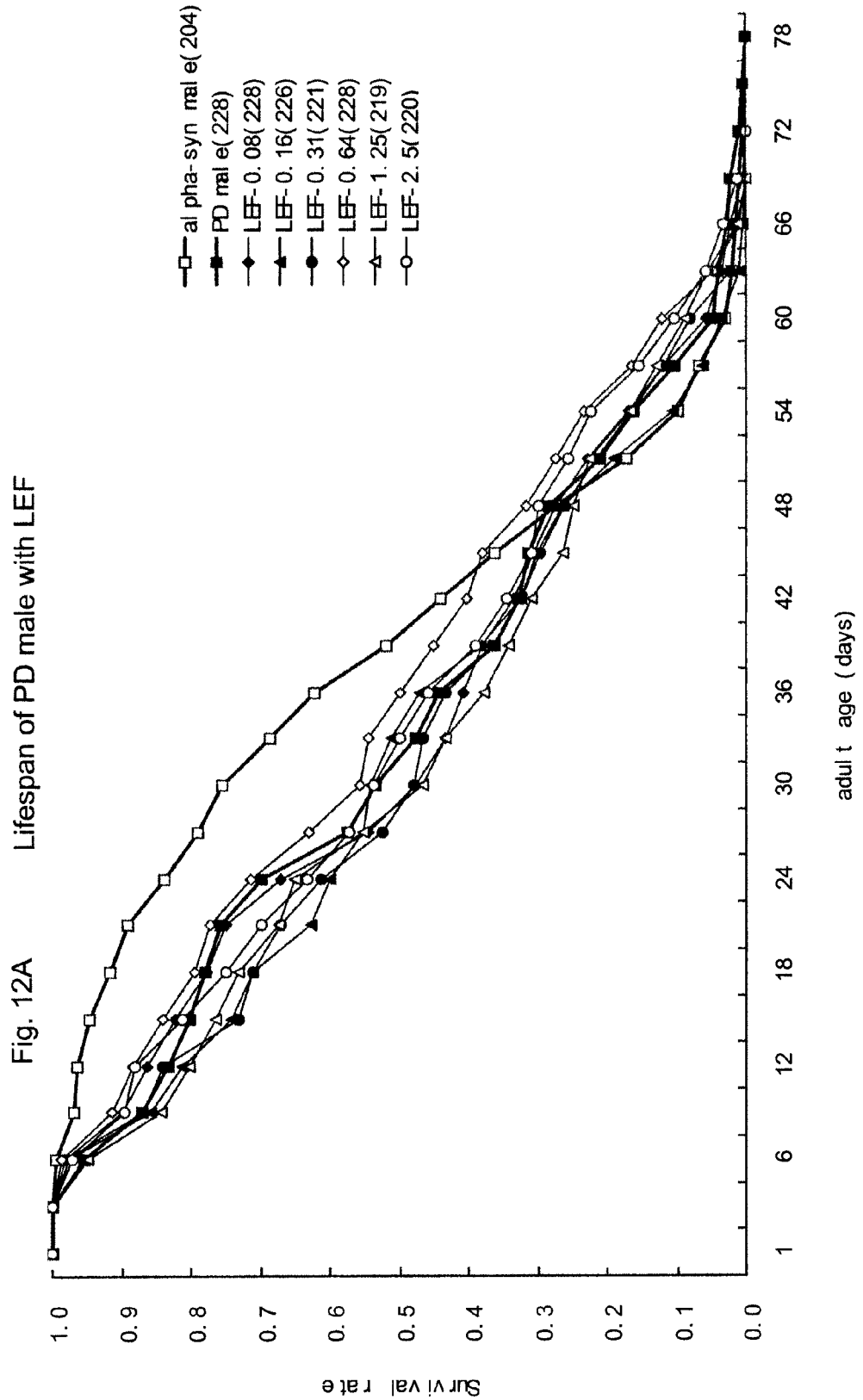
Fig. 12A  Lifespan of PD male with LEF

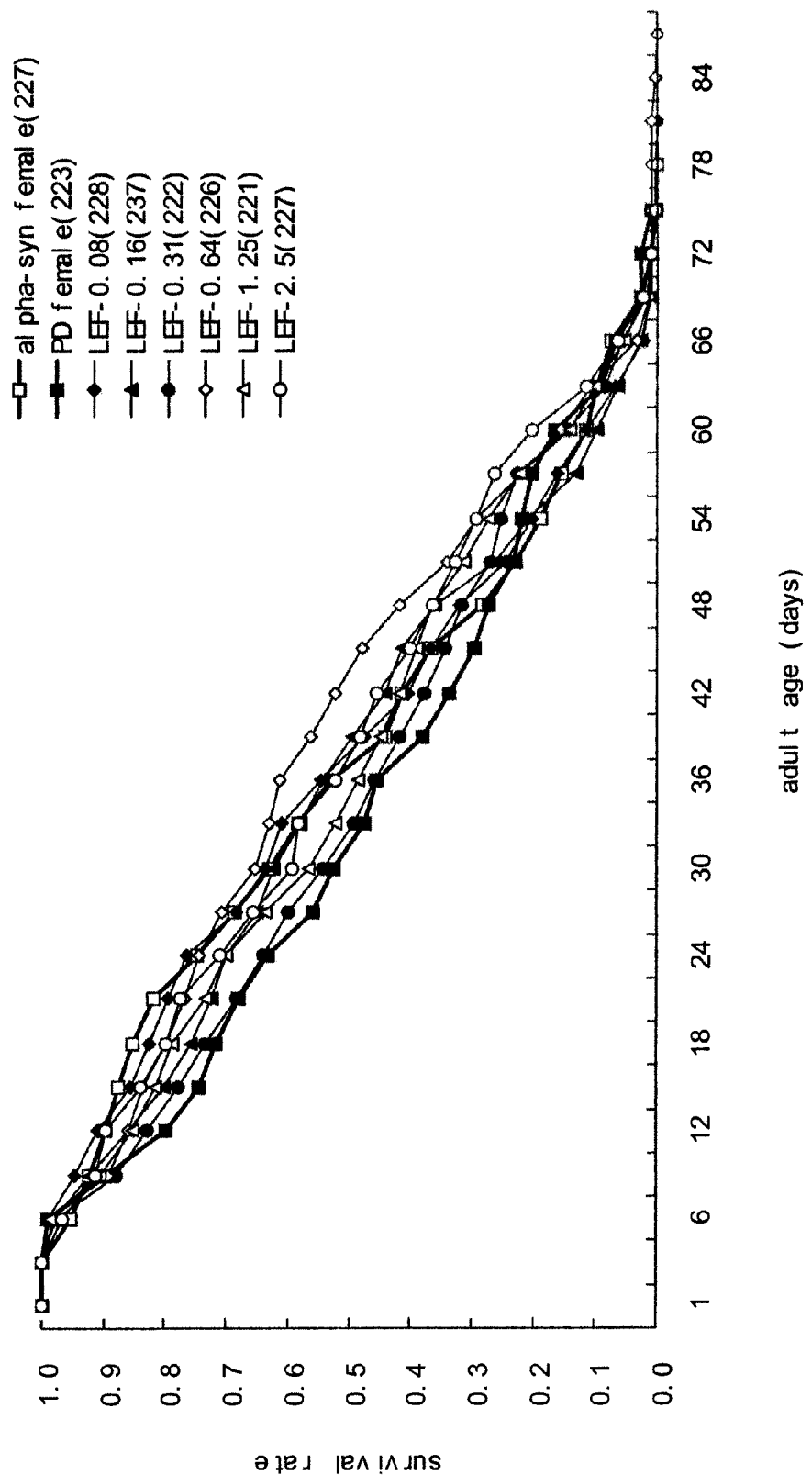
Fig. 12B  Lifespan of PD female with LEF

METHODS FOR TESTING FOR CALORIC RESTRICTION (CR) MIMETICS

CROSS REFERENCE TO RELATED APPLICATIONS

This patent application is a divisional of application Ser. No. 11/377,986 filed on Mar. 17, 2006 and entitled, Methods for Testing for Caloric Restriction (CR) Mimetics.

BACKGROUND OF THE INVENTION

1. Field

The present disclosure relates to the fields of medical and biological research and methods for discovering medical therapeutic treatments and methods for treating certain diseases and/or ailments. Certain aspects of this disclosure relate to properties of and uses of grape extract and substances related to grape extract.

2. Background

Grape extract has been studied for its use as a possible dietary supplement and has been available commercially from a variety of sources. For example, a form of grape extract called Regrapex-R is available from Interpharma Praha, a.s., of the Czech Republic. Regrapex-R is a whole extract from red grapes of *Vitis vinifera*, grown in southern France, and contains a natural resveratrol complex derived from dried roots of *Polygonum cuspidatum*. Other forms of grape extract include grape seed extracts which are commercially available.

Examples of uses of grape extract are shown in U.S. Pat. Nos. 6,470,894 and 6,638,545. U.S. Pat. No. 6,470,894 describes a composition for inclusion within a cigarette, cigar, pipe or smokeless tobacco, and this composition is an antioxidant complex which is capable of scavenging and neutralizing the free radicals emanating from the burning or heated tobacco. This composition includes glutathione, green tea and/or grape seed extract. U.S. Pat. No. 6,638,545 describes the use of grape extract as a food complement to treat obesity and to treat, for cosmetic purposes, cellulite. The grape extract is obtained from grape seeds or grape marc. Other uses of grape extract are described in published U.S. Patent Applications 2005/0100617 and 2004/0047896.

The grape extract "Regrapex-R" includes resveratrol which has been thought to be a possible caloric restriction (CR) mimetic. CR is a technique in which subjects, such as mice or humans, are fed a diet ("a CR diet") which has less than a "normal" amount of food for at least a certain period of time. Typically, the amount of food given in the CR diet is less than about 50% or 40% of the minimum recommended daily amount measured in calories. The effects of a CR diet have been extensively studied, and numerous researchers have developed techniques to screen for interventions, such as therapeutic substances or compounds, which when administered to a subject on a normal diet tend to cause the subject's physiological or biological state to mimic the state of an organism on a CR diet. Such interventions are referred to as CR mimetics because they cause the biological state of the organism receiving the intervention to mimic the state of a similar organism on a CR diet even if the organism is not on a CR diet. The effects of CR diets and techniques for screening for CR mimetics are described in the following patents and published applications which are hereby incorporated herein by reference: U.S. Pat. Nos. 6,406,853 and 6,569,624 and U.S. published applications 2005/0266438, 2005/0013776, 2004/0191775, 2004/0180003, 2003/0224360 and 2003/0124540.

SUMMARY OF THE DESCRIPTION

Methods for testing CR mimetics and potential CR mimetics (e.g. "candidate CR mimetics") are described. The methods may be employed as part of a battery of tests (e.g. a set of tests) to screen for potential CR mimetics and to characterize the properties of CR mimetics and potential CR mimetics. This battery of tests may include testing for antioxidant capabilities of a potential CR mimetic and/or testing the effect of administering the potential CR mimetic to a transgenic animal. Another aspect of the present disclosure relates to the use of grape extract to treat neurological disorders, diseases and/or ailments such as Parkinson's disease in humans.

In one exemplary method described herein, a method for testing a CR mimetic or CR mimetic candidate includes administering the CR mimetic or CR mimetic candidate to a transgenic animal and determining the effects of the administering. This testing may be performed for the purpose of determining whether the CR mimetic candidate is in fact a CR mimetic or may be performed to determine the characteristics or properties of the CR mimetic candidate. The transgenic animal typically includes an added gene from another type (e.g. species) of animal or a modified gene which is designed to produce a disease or ailment of the another type of animal in the transgenic animal. The effects of the administering may include an improvement in a symptom of the disease. In a specific example provided below, administering of grape extract to a transgenic *Drosophila* Parkinson's disease (PD) model was shown to improve the symptoms of PD in the male *Drosophila* receiving the grape extract; in particular, grape extract given to male *Drosphila* having the PD gene was shown to protect against a decline in climbing rate with age. This administering may be part of a set of screening tests which are designed to determine whether a CR mimetic candidate is a CR mimetic; for example, another screening test may include comparing levels of biological parameters of known CR markers to measurements of the known CR markers from the subject having been administered the CR mimetic candidate. In the specific example provided below, grape extract may be tested as a CR mimetic by obtaining measurements of gene expression levels (e.g. RNA transcript levels) of known CR markers in subjects receiving the grape extract and comparing those measurements to known gene expression levels, induced by a CR diet, of the known CR markers. Known CR markers include genes known to be affected (e.g. affected in gene expression levels) by a CR diet or a known CR mimetic or gene products of such genes or metabolites involved in biochemical pathways which use those gene products.

Another aspect of the present disclosure relates to testing of the antioxidant properties of a CR mimetic or potential CR mimetic. The antioxidant properties of the CR mimetic or potential CR mimetic may be compared to known antioxidants, and this testing may be part of a set of tests designed to determine whether a potential CR mimetic is a CR mimetic (or to characterize the CR mimetic); for example, the potential CR mimetic, which has been or will be tested for antioxidant capabilities, may be tested using known CR mimetic screening techniques, such as those described in U.S. Pat. Nos. 6,406,853 and 6,569,624 and in U.S. published applications 2005/0266438, 2005/0013776, 2004/0191775, 2004/

0180003, 2003/0224360, and 2003/0124540, to determine whether the potential CR mimetic is a CR mimetic.

BRIEF DESCRIPTION OF THE DRAWINGS

The present disclosure is illustrated by way of example and not limitation in the figures of the accompanying drawings in which like references indicate similar elements.

FIG. 1 is a flowchart showing an exemplary method of using a transgenic animal for tests of a CR mimetic or CR mimetic candidate.

FIG. 2 is a flowchart showing an exemplary method of testing a known CR mimetic or a CR mimetic candidate for antioxidant capabilities.

FIG. 3 is a flowchart showing an exemplary method for treating a neurological disease or ailment.

FIG. 5A shows an ESR spectra which shows the free radical savengering capabilities of a form of grape extract on superoxide radicals.

FIG. 5B is a graph showing the free radical scavengering capabilities, on superoxide radicals, of a form of grape extract.

FIG. 7 is a table which compares the free radical scavenging capabilities of a form of grape extract, labeled as "LEF," with other well known scavengers, including a combination of vitamins C and E (which is labeled as "EPCK1").

FIG. 10B is a chart which shows a statistical analysis of the data from the climbing assay shown in FIG. 10A.

FIG. 11A is a graph which shows the effect of a form of grape extract on the climbing ability of female transgenic *Drosophila* that have the PD gene.

FIG. 11B is a chart which shows a statistical analysis of the data from the climbing assay shown in FIG. 11A.

FIG. 12A is a graph that shows the effect of a form of grape extract on lifespan for male *Drosophila*.

FIG. 12B is a graph that shows the effect of a form of grape extract on lifespan for female *Drosophila*.

DETAILED DESCRIPTION OF THE INVENTION

Figure 4B:
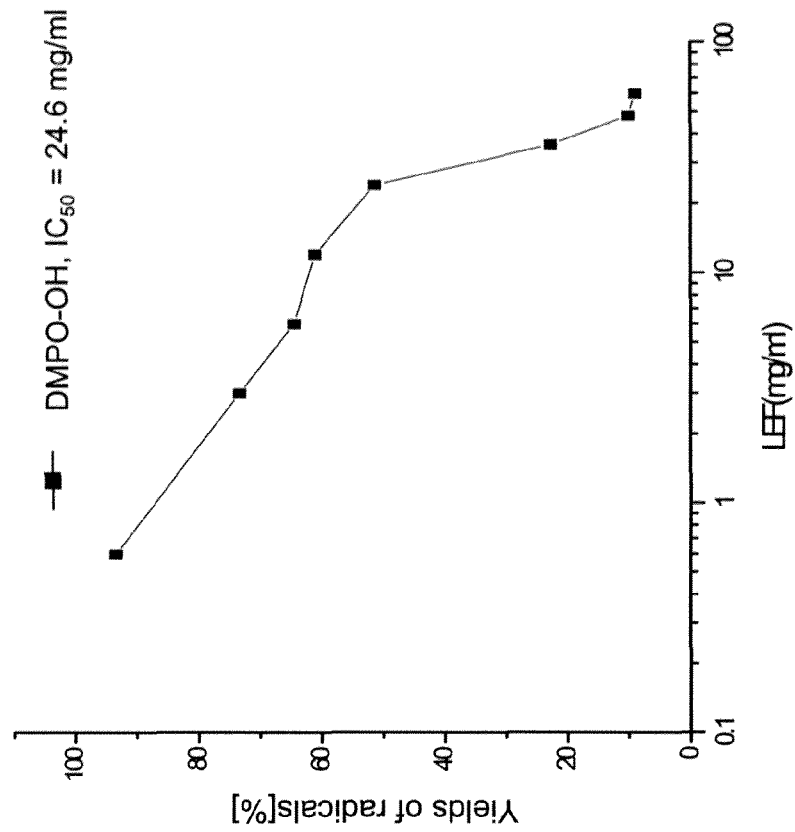
FIG. 4B is a graph showing the free radical scavengering capabilities, on hydroxyl radicals, of a form of grape extract.

The various embodiments of the present inventions will be described with reference to numerous details set forth below, and the accompanying drawings will illustrate these various embodiments. The following description and drawings are illustrative of the invention and are not to be construed as limiting the invention. Numerous specific details are described to provide a thorough understanding of the present inventions. However, in certain instances, well known or conventional details are not described in order to not unnecessarily obscure the present inventions in detail.

Exemplary embodiments are described with reference to specific configuration and techniques. Certain embodiments of the present invention pertain to methods of screening for CR mimetics and reproducing the effects induced by a CR diet without requiring the subject to endure an actual CR diet. Methods of identifying compounds that reproduce the effects induced by CR, identifying compounds that prevent or delay the onset of age related diseases or extend longevity, and extending longevity in mammals are disclosed.

Currently, CR when started either early in life or in middle-age, represents the best established paradigm of aging retardation in mammals. See for example, Weindruch, et. al., *The Retardation of Aging and Disease by Dietary Restriction*, C. C. Thomas, Springfield, Ill., 1988. The effects of CR on age-related parameters are broad. CR increases maximum lifespan, reduces and delays the onset of age related diseases, reduces and delays spontaneous and induced carcinogenesis, suppresses autoimmunity and general decline of immune function associated with aging, and reduces the incidence of several age-induced diseases (Weindruch, supra, 1988). For example, CR delays the onset kidney disease, cancer, autoimmune disease, and diabetes. CR reduces neuronal loss with age in mouse models of neurodegenerative disorders, including Parkinson's disease and Alzheimer's disease. CR also prevents decline in learning ability with age as measured by psychomotor and spatial memory tasks. CR also prevents dendritic spine loss and enhances the brain's plasticity and repair.

Even though CR brings many beneficial effects to animals and humans, it is not likely that many will avail themselves of a CR lifestyle. As is known, it is difficult for any animal or human to maintain a diet program similar to a CR diet program. There is thus a need to identify, evaluate, and develop CR mimetic compounds or drugs that are capable of mimicking at least some of the anti-aging, anti-disease effects, and other beneficial effects of CR without the reduction of dietary calorie intake as required by CR diet programs. Furthermore, it is an aspect of at least certain embodiments of the invention to use a battery of tests (e.g. a set of tests) which are used to search for and screen for a CR mimetic from a pool of CR mimetic candidates. This battery of tests may include the conventional testing of gene expression levels or other techniques for screening for CR mimetics (e.g. as described in U.S. Pat. Nos. 6,406,853 and 6,569,624 and U.S. published applications 2005/0266438, 2005/0013776, 2004/0191775, 2004/0180003, 2003/0224360 and 2003/0124540) with other tests such as tests for antioxidant capabilities, and/or test on effects of mitochondria, and/or tests of the effects of administering a CR mimetic candidate to a transgenic animal. For example, a transgenic animal which is created to have a genetically designed model of an aging disease, such as Parkinson's disease or Alzheimer's disease or other disease(s) commonly associated with age (e.g. certain types of diabetes or cancers), may be used in a test which studies the effects of administering a CR mimetic candidate to such a transgenic animal.

FIG. 1 shows an example of a method, according to one exemplary embodiment of the present inventions, which uses a transgenic organism (such as transgenic animal or plant or other life forms) in a study of a known CR mimetic or a CR mimetic candidate (e.g. a study to screen for a CR mimetic candidate). Operation 101, in FIG. 1, involves the selection of a type of a transgenic animal for use in the CR mimetic study.

The transgenic animal typically includes an added gene from another type of animal or a modified gene which is designed to produce a disease or ailment of another type of animal in the transgenic animal. In the specific example described herein, Parkinson's disease (PD) model *Drosophila* were selected for use with a CR mimetic candidate, a form of grape extract. Further details regarding the Parkinson's disease model *Drosophila* and the particular form of grape extract are provided below. In operation 103, a known CR mimetic or a CR mimetic candidate is administered to the selected transgenic animal (e.g. a Parkinson's disease model *Drosophila*). Then in operation 105, the effects of the administering of the known CR mimetic or a CR mimetic or a CR mimetic candidate to the transgenic animal are determined. FIGS. 10A, 10B, 11A, and 11B show the results of determining the effects of such administering of a form of grape extract to a Parkinson's disease model *Drosophila*. It appears, from these specific results, that grape extract is effective in reducing the effects of Parkinson's disease, at least in the male portion of a population. These results extend to humans because the particular Parkinson's disease model *Drosophila* were designed as a transgenic animal to model human Parkinson's disease, and thus these results show that grape extract may be used to treat, in humans, neurological diseases, such as Parkinson's disease. Operation 107 is an optional operation which performs other tests using the CR mimetic candidate to verify whether the candidate is a CR mimetic. These additional tests may include conventional screening for CR mimetic candidates such as assaying of biological parameters, such as gene expression levels (e.g. RNA transcript levels), of certain CR markers, and the comparing of those measured gene expression levels to measured gene expression levels of those CR markers of subjects on a CR diet or a known CR mimetic. See for example, U.S. Pat. Nos. 6,406,853 and 6,569,624 and U.S. published applications 2005/0266438, 2005/0013776, 2004/0191775, 2004/0180003, 2003/0224360 and 2003/0124540. CR markers include genes (and hence expressed gene levels as measured by concentrations of RNA transcripts) which are known to be affected by a CR diet (based on the studies of the differential effect of CR diets relative to normal diets) or by a known CR mimetic or gene products (e.g. proteins) of such genes or metabolites involved in biochemical pathways which use those gene products.

FIG. 2 shows an example of a method, according to another exemplary embodiment of the present inventions, which studies the antioxidant capabilities of a known CR mimetic or a CR mimetic candidate. FIGS. 4A, 4B, 5A, 5B, 6A, 6B and 7 show specific examples, which are discussed further below of studies which determine antioxidant capabilities of a CR mimetic candidate. Alternative methods may study the protective effects of a CR mimetic candidate on mitochondrial functions, and specific examples of these alternative methods are shown in FIGS. 8A, 8B, 9A and 9B. Referring to FIG. 2, operation 201 selects a known CR mimetic or a potential CR mimetic ("CR mimetic candidate"), and in operation 203, the antioxidant capabilities of the selected CR mimetic or CR mimetic candidate are determined. Then in optional operation 205, the determined antioxidant capabilities are compared to known antioxidants; FIG. 7 shows an example of such a comparison. The method shown in FIG. 2 may also optionally include operation 207, in which other tests are performed to determine whether the CR mimetic candidate tested in operation 203 appears to be a CR mimetic. In other words, operation 207 performs other tests, such as conventional CR mimetic screening tests (e.g. as described in U.S. Pat. Nos. 6,406,853 and 6,569,624) or the testing of operations 101, 103, and 105 of FIG. 1 or the lifespan testing shown in FIGS. 12A and 12B. These tests, if performed, faun a set of tests for testing and screening a CR mimetic candidate as part of a process of identifying a CR mimetic from a pool of CR mimetic candidates.

FIG. 3 relates to another aspect of the present inventions. This aspect involves the treatment of neurological diseases or ailments, such as Parkinson's disease or Alzheimer's disease. The particular method shown in FIG. 3 has been used to treat Parkinson's disease model *Drosophila* as is shown in FIGS. 10A, 10B, 11A, and 11B. Operation 301 of FIG. 3 involves determining that a particular subject (e.g. a human patient) has a neurological disease or ailment (e.g. the human patient has Parkinson's disease). A therapeutically effective amount of grape extract (e.g. Regrapex-R) is then administered to the subject (e.g. the human patient who has Parkinson's disease). The amount may be determined based on its effect by monitoring the effect in operation 305. In other words, the amount may be varied to determine whether a current amount has a beneficial effect and if not the current amount can be increased or decreased. It is anticipated that effects will be observed for an average subject when the ratio between the mass of food consumed in one day and the mass of grape extract (in the form of Regrapex-R) given in one day is about 2000 to 1 (or about 1-2 g per day for an average adult weighing between 120-200 lbs.). More details will now be provided for the PD *Drosophila* model and the tests which produced the results shown in FIGS. 10A, 10B, 11A, 11B, 12A and 12B.

The form of grape extract which was used to produce the results described herein is a commercially available form of grape extract known as "Regrapex-R" which is available from Interpharma Praha, a.s. of the Czech Republic. Regrapex-R is described on Interpharma's website (http://www.interpharma-praha.com). Regrapex-R is a whole grape (*vitis virnfera*) extract enriched with purified powdered extract, containing resveratrol, from dried roots of *Polygonum cuspidatum*; one gram of bulk Regrapex-R consists of about 800 mg whole grape extract and 200 mg of dried root powder from *Polygonum cuspidatum*. This product contains concentrated active principles found in red grapes (simple polyphenols, flavonoids, anthocyanins and OPC's).

The *Drosophila* studies shown in FIGS. 10A, 10B, 11A, 11B, 12A and 12B use a transgenic *Drosophila* having been genetically engineered to have certain added genes which produce a phenotype which resembles Parkinson's disease in humans. This type of *Drosophila* is referred to as a Parkinson's disease (PD) *Drosophila* model. Transgenic alpha-synuclein *Drosophila* were obtained from Dr. Feany at Harvard University (Feany and Bender, 2000). The Parkinson's disease model flies express a human form of alpha-synuclein and produce adult-onset loss of dopaminergic neurons, filamentous intraneuronal inclusions containing alpha-synuclein and locomotor dysfunction. Since this *Drosophila* model recapitulates the essential features of the human disorder, it makes possible a powerful genetic approach to study Parkinson's disease in humans.

The control non-PD flies (UAS-wild-type alpha-synuclein/+) and PD flies (Ddc-GAL4/+; UAS-wild-type alpha-synuclein/+) were maintained at 25° C. on a 12-h light/dark cycle in bottles containing an agar, corn meal, sucrose, water, and dried yeast medium (Pendleton et al., 2002). Propionic acid was added to prevent fungal growth. Drugs (Regrapex-R) were added to the medium at the final concentrations marked in the results (e.g. the grape extract, labeled "LEF," dose is mg/100 g culture medium, so "LEF-1.25" in FIGS. 10A-12B means 1.25 mg of Regrapex-R per 100 g of culture medium) and the mixture was heated to a boil with continuous stirring. UAS-wild-type alpha-synuclein flies were used as the basis for comparison with the PD flies because they are female parent of PD flies and a genetically steady, constant breeding stock whose functional behavior in our standard locomotor assay described below was identical with the transgenic stock during the first 6 or 12 days after eclosion.

Flasks containing the desired stocks were emptied leaving pupa to emerge (eclose) as adults. Newly eclosed flies of both the non-PD control and PD strains were placed in culture tubes (10 flies per tube) that contained drug-treated food which are renewed every 3 days. Control organisms were treated similarly except that the medium was drug free. The following day, the number of dead flies is recorded at 3-day intervals. At 6-day intervals thereafter, the adults were tested in the climbing assay. Assays continued until day 48.

Climbing Assay

The climbing assay was performed as described (Feany and Bender, 2000; Pendleton et al., 2002). Ten flies were placed in an empty vitreous 110×27-mm vial, around which a horizontal line 80 mm above the bottom of the vial was drawn. After the flies had acclimated for 10 min at room temperature, every group was assayed at random, to a total of 10 trials for each. The procedure involved gently tapping the flies down to the bottom of the vial. The number of flies above the mark of the vial was counted after 10s of climbing, and repeated for 10 times to get the mean number of flies above the mark in the vial. These values were then averaged, and a group mean and standard error were obtained. The resulting mean was used as the overall value, and the exponent of climbing ability was determined for each single group of flies on a particular day. Where appropriate, the mean values of the various fly groups were statistically compared using Student's t test. All climbing assays were performed in an isolation room at 25° C., 60-70% humidity under standard lighting conditions.

Figure 10A:
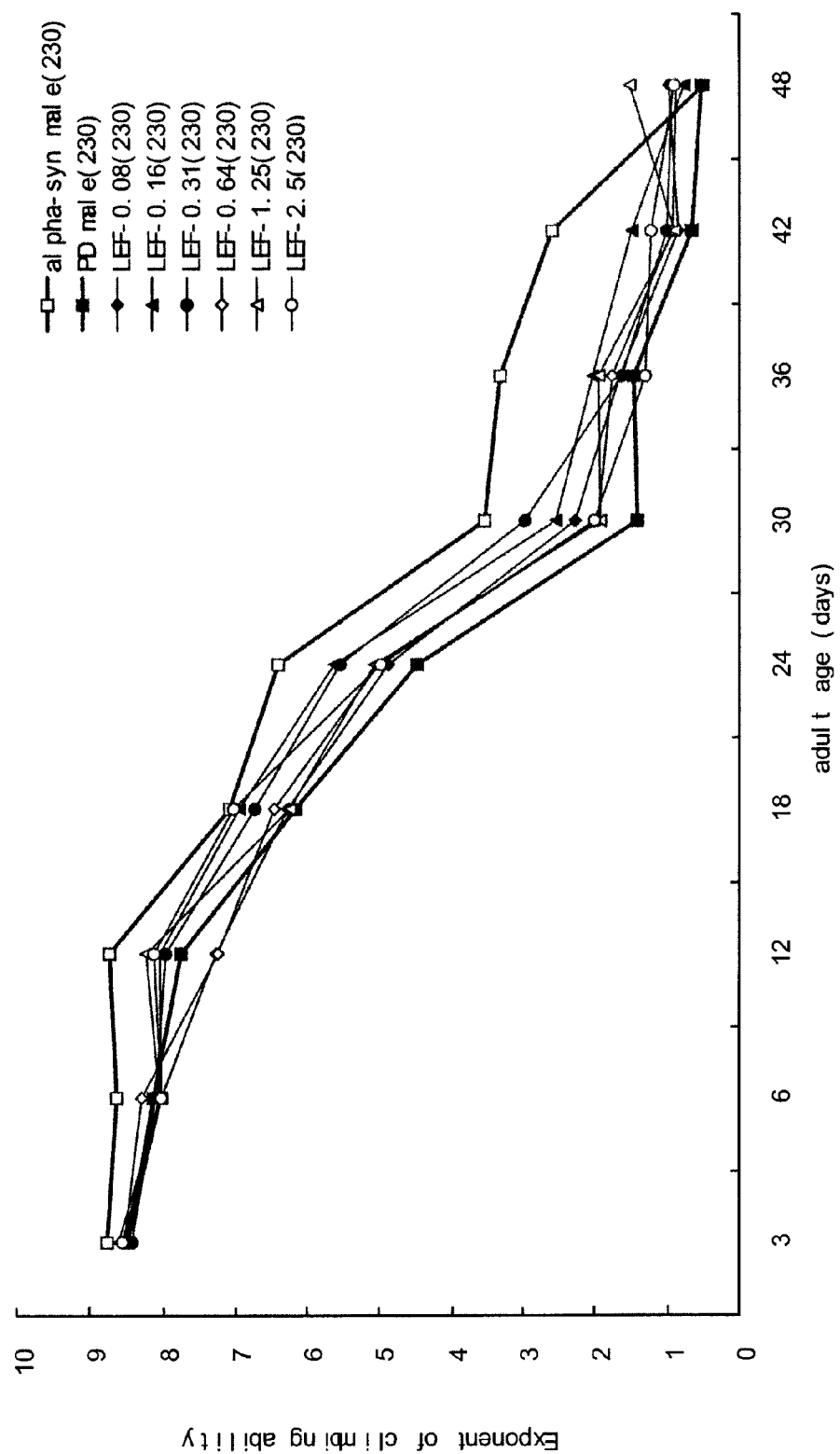
FIG. 10A is a graph which shows the effect of a form of grape extract on the climbing ability of male transgenic *Drosophila* that have the PD gene.

The results of the climbing assay (shown in FIGS. 10A, 10B, 11A, and 11B) show that, at least for the male PD *Drosophila* model, the administered grape extract shows a positive effect (e.g. delayed onset of loss of climbing ability relative to male PD *Drosophila* model ("PD male") which did not receive the grape extract "drug"). FIG. 10A shows the result of a climbing assay using male control *Drosophila* ("alpha syn male" which do not express the human alpha synuclein gene since they lack the promoter for this transgene), "PD male" *Drosophila* (without receiving grape extract), and male PD *Drosophila* having received varying levels of grape extract (from 0.08 mg of Regrapex-R/100 g of culture medium to 2.5 mg of Regrapex-R/100 g of culture medium). FIG. 10B shows a statistical analysis of the effect of administered grape extract on climbing response (from the data shown in FIG. 10A) in male *Drosophila*. These in vivo assays show that, at least for male *Drosophila*, the administered grape extract ameliorated the loss of motor function associated with Parkinson's Disease and an improvement in the climbing ability compared to the PD male *Drosophila* that were not administered the grape extract. FIG. 11A shows the result of a climbing assay using female control *Drosophila* ("alpha syn female"), "PD female" *Drosophila* (without receiving grape extract) and female PD *Drosophila* having received varying levels of grape extract (from 0.08 mg of Regrapex-R/100 g of culture medium to 2.5 mg of Regrapex-R/100 g of culture medium). FIG. 11B shows a statistical analysis of the effect of administered grape extract on climbing response (from the data shown in FIG. 11A) in female *Drosophila*. These in vivo assays appear to show that, at least for female *Drosophila*, the administered grape extract had no beneficial effect on the climbing ability of female PD *Drosophila*.

A lifespan study was also performed on the PD *Drosophila* lines; the results of this study are shown in FIGS. 12A and 12B. Again, the PD *Drosophila* (male and female) were either given no grape extract (a PD *Drosophila* control) or grape extract at a certain dosage (e.g. "LEF-1.25" meaning the culture medium for PD *Drosophila* receiving this dose had 1.25 mg of Regrapex-R per 100/g of culture medium). The normal *Drosophila* ("alpha syn male or female" transgenic *Drosophila* for human alpha synuclein but lacking a promoter and thus not expressing alpha synuclein) were also included in this study. It appears that, to at least some extent, the grape extract acts as a CR mimetic, to the extent it increases lifespan in the female PD *Drosophila* model.

Another aspect of the inventions related to in vitro studies of the antioxidant capabilities (shown in FIGS. 4A-7) of grape extract and the ability of grape extract to protect mitochondria (shown in FIGS. 8A-9B). As noted above, these in vitro studies (of one or both types) may be part of a battery of tests on a CR mimetic candidate, and this battery may include tests with one or more transgenic animals (e.g. as shown in FIG. 1 and described herein) and may include conventional gene expression level comparisons showing RNA transcript levels of selected CR markers for a first subject on a CR diet and a second subject, of the same species as the first subject, being administered the CR mimetic candidate, but on a normal diet. This battery of tests may be used to screen for CR mimetics from a pool of CR mimetic candidates.

Figure 4A:
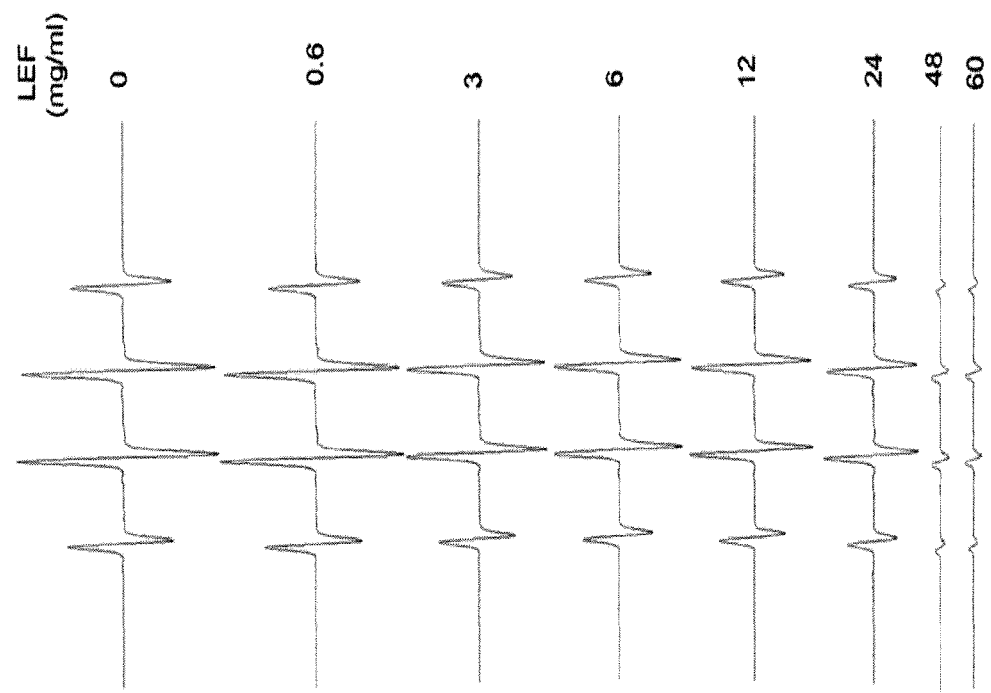
FIG. 4A shows an electron spin resonance (ESR) spectra of hydroxyl radicals which shows the free radical scavengering capabilities of a form of grape extract on hydroxyl radicals.
Figure 6B:
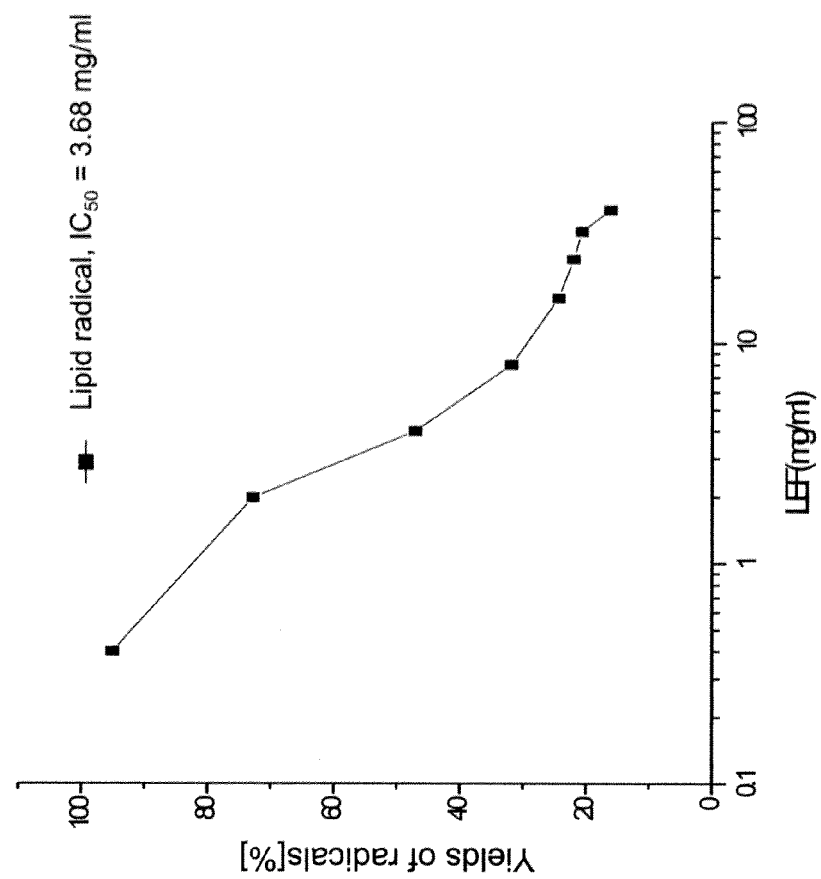
FIG. 6B is a graph showing the free radical scavengering capabilities, on lipid radicals of a form of grape extract.
Figure 6A:
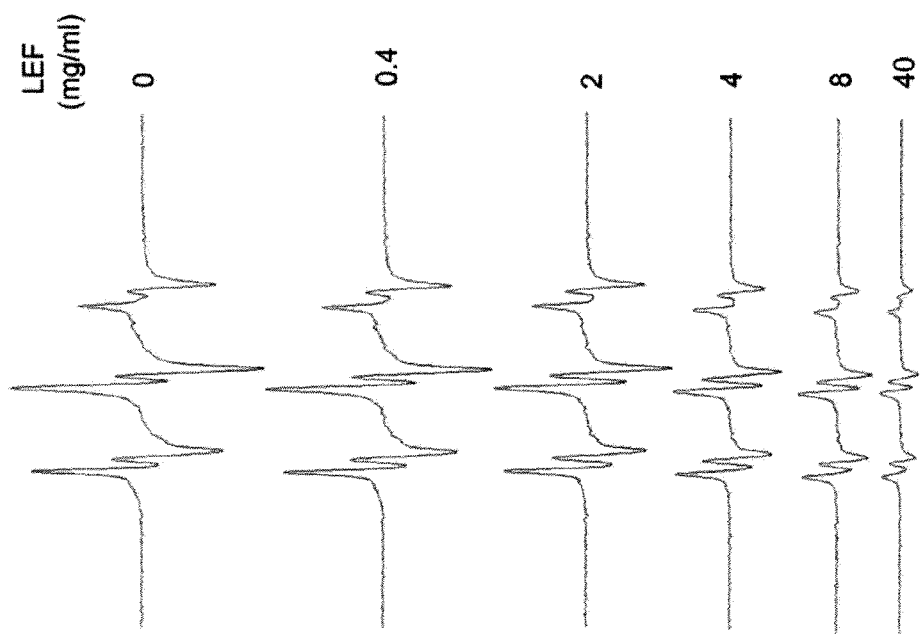
FIG. 6A shows an ESR spectra which shows the free radical scavengering capabilities of a form of grape extract on lipid radicals.
Figure 8A:
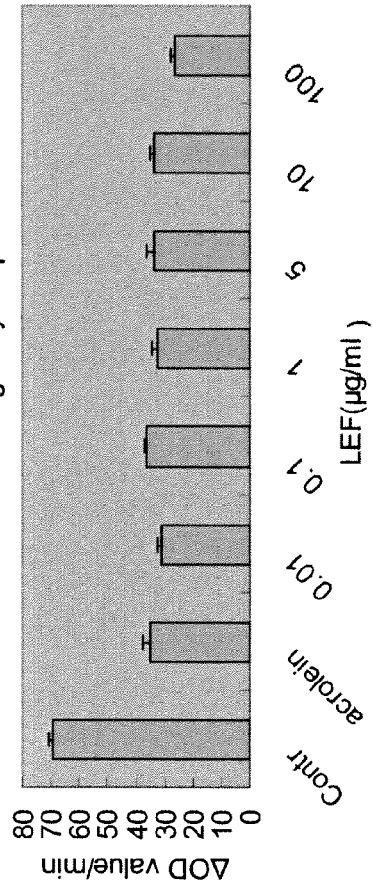
FIG. 8A and 8B show the effect of a form of grape extract on acrolein-induced decrease in mitochondrial complex II activity in liver and brain mitochondria respectively.
Figure 8B:
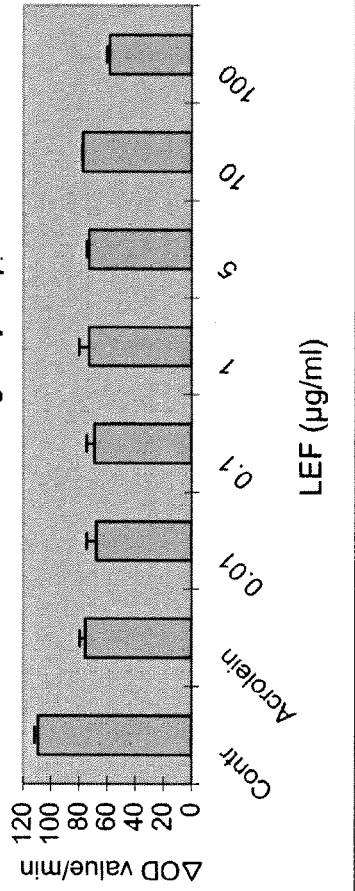
Figure 9A:
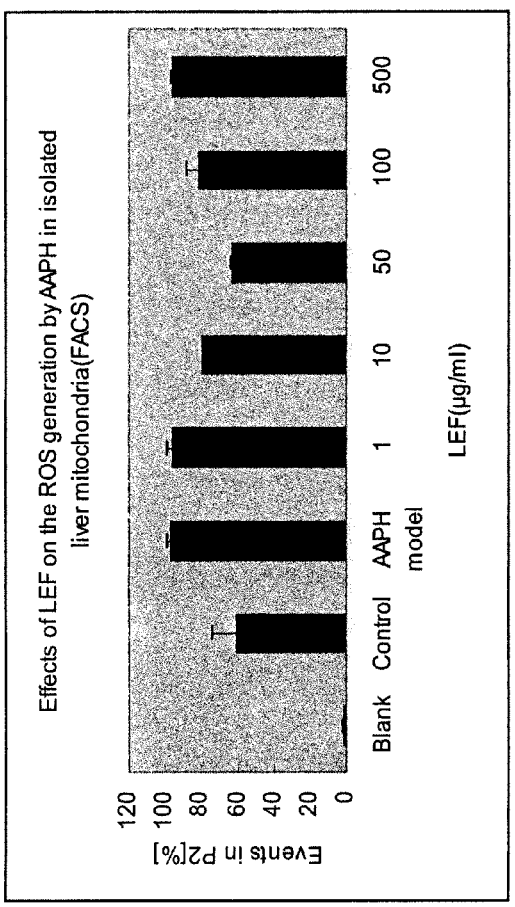
FIG. 9A and 9B show the effect of a form of grape extract on AAPH (a radical initiator that with increasing concentration represses state 3 respiration) induced decrease in mitochondrial complex I activity in liver and brain mitochondria respectively.
Figure 9B:
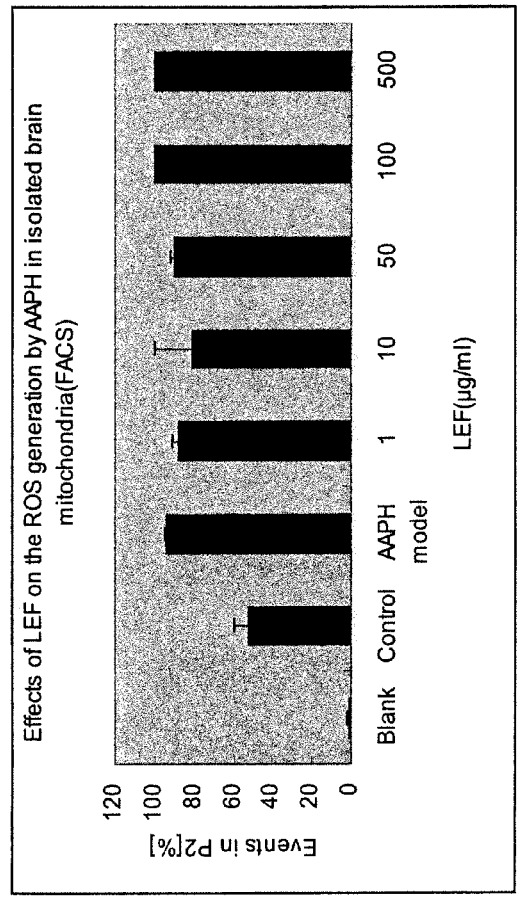

As shown in FIGS. 4A-7, grape extract (in this case Regrapex-R) effectively scavenged hydroxyl, superoxide, and lipid free radicals. The results of the scavenging of hydroxyl radicals by this grape extract are shown in FIGS. 4A and 4B and the results of the scavenging of superoxide radicals by this grape extract are shown in FIGS. 5A and 5B, and the results of the scavenging of lipid radicals by this grape extract are shown in FIGS. 6A and 6B. In all cases, the effect of this grape extract on the different types of free radicals was detected using spin trapping agents (such as DMPO) with an electron spin resonance (ESR) spectrometer. (See Liu and Mori, 1992; Liu and Mori, 1993; and Liu and Mori, 1993). The grape extract was prepared in several different concentrations in DMSO (dimethyl sulfoxide) as shown in FIGS. 4A-6B; in each case the amount of Regrapex-R in DMSO is in mg of Regrapex-R per ml) of DMSO. FIGS. 4A and 4B show a dose dependent scavenging effect on the hydroxyl radical with an $IC_{50}$ of 24.6 mg/ml. This compares favorably to a potent hydroxyl radical scavenger made by combining vitamin C with vitamin E (referred to as EPCK1 in FIG. 7). FIGS. 5A and 5B show a dose dependent scavenging effect on superoxide radicals with an $IC_{50}$ 0.0026 mg/ml. FIGS. 6A and 6B show a dose dependent scavenging effect on lipid radicals with an $IC_{50}$ of 3.68 mg/ml; this scavenging effect of grape extract is similar to EPCK1 as shown in FIG. 7 which shows a comparison of this fool' of grape extract (Regrapex-R), labeled as LEF, with a variety of known free radical scavengers, including ALC (Acetyl-L-Caritine), LA (∝-lipoic acid), EPCK1 (a diester of alpha-tocopherol (vitamin E) and ascorbic acid (vitamin C), Resv (Resveratrol), UTR and C-Med (both formulations of "cats claw extract").

FIGS. 8A-9B show the results of tests to investigate the ability of a form of grape extract (Regrapex-R, in this case) to protect mitochondria from oxidative damage. At least in the results of FIG. 9A, grape extract showed some ability to protect mitochondria from chemically induced oxidative damage. The mitochondria were prepared in the following manner: Male Sprague Dawley rats (180-200 g) were purchased from Shanghai SLAC Laboratory Animal Co. Ltd (Shanghai, China). The animals were terminated by decapitation after an overnight fast and livers were removed for immediate mitochondrial isolation. Mitochondria were isolated as described {Krahenbuhl, 1991} with slight modification. Briefly, tissues were rinsed with saline, weighed, and put into ice-cold isolation buffer containing 0.25 M sucrose, 10 mM Tris, 0.5 mM EDTA, pH 7.4. Tissues were sheared carefully to mince, and rinsed to get rid of residual blood, and then homogenized in 2.5 vol of isolation buffer. The homogenate was adjusted to 8 vol with isolation buffer and centrifuged at 1,000 g for 10 min; the supernatant fraction was decanted and saved. The pellet was washed once with 2 vol of isolation buffer. The supernatant fractions were combined and centrifuged at 10,000 g for 10 min. The mitochondrial pellet was washed twice with isolation buffer. All above operations were carried out at 4° C. The mitochondrial protein concentration was determined using the BCA™ Protein Assay kit (Pierce 23225) using bovine serum albumin (BSA) as a standard. Freshly isolated mitochondria were either used immediately for respiration and permeability transition assays, or stored at −80° C. until enzyme analysis. After isolation and preparation, the mitochondria were exposed to acrolein (in the case of the tests shown in FIGS. 8A and 8B) or to AAPH (in the case of the tests shown in FIGS. 9A and 9B). Acrolein's effect on isolated mitochondria has been described by M. J. Picklo and T. J. Montine in "Acrolein inhibits respiration in isolated brain mitochondria." Biochem Biophys. Acta, 2001, Feb. 14, 1535 (2), pages 145-152. AAPH's effect on mitochondria has been described by T. Kanno, et al., in "Dysfunction of mouse liver mitochondria induced by 2,2'-azobis-(2-amidinopropane) dihydrochloride, a radical initiator, in vitro and in vivo." Free Radical Res., 1994 September; 21(4), pages 223-234. In the case of the tests shown in FIGS. 8A and 8B, grape extract showed no apparent protective effect against acrolein induced oxidative damage of both types (liver and brain) mitochondria. In the case of the tests shown in FIGS. 9A and 9B, gape extract showed (in liver mitochondria but not brain mitochondria) a dose dependent inhibition on AAPH induced damage at 10 and 50 μg/ml but the inhibitory effect was lost at higher concentrations.

While particular embodiments of the inventions have been shown and described, it will be appreciated that changes and modifications can be made without departing from the inventions in their broader aspects, and therefore the following claims are to encompass within their scope all such changes and modifications.

The invention claimed is:

1. A method of determining effects of administering a Caloric Restriction (CR) mimetic or a CR mimetic candidate to a non-mammalian transgenic organism, the method comprising:
    administering at least one of the CR mimetic or the CR mimetic candidate to the non-mammalian transgenic organism, the non-mammalian transgenic organism comprising a transgene designed to produce a disease or ailment in the non-mammalian transgenic organism;
    determining the effects of the administering wherein the determining comprises determining whether the administering improves the disease or ailment; and
    performing a plurality of other tests using the at least one of the CR mimetic or the CR mimetic candidate, wherein at least one of the plurality of other tests comprises determining a protective effect of the CR mimetic or the CR mimetic candidate against oxidative damage to mitochondria by (1) inducing oxidative damage to the mitochondria, (2) administering an amount of the CR mimetic or the CR mimetic candidate sufficient to inhibit the induced oxidative damage in the mitochondria, and (3) evaluating the effect of the CR mimetic or the CR mimetic candidate on mitochondrial complex activity.

2. The method of claim 1 wherein only the CR mimetic candidate is administered in the administering and wherein determining comprises determining whether the effects of the administering indicate that the CR mimetic candidate is a CR mimetic.

3. The method of claim 1 wherein the transgenic non-mammalian organism is a transgenic fly and the transgene is an added gene from another type of animal or a modified gene designed to produce a disease or ailment of the another type of animal in the transgenic fly.

4. The method of claim 3 wherein the transgenic fly has a symptom of the disease or ailment.

5. The method of claim 4 wherein only the CR mimetic candidate is administered in the administering and wherein the method further comprises:
    comparing levels of biological parameters of known CR markers to measurements of the known CR markers from subjects having been administered the CR mimetic candidate.

6. The method of claim 1 wherein the administering comprises administering a grape extract.

7. The method of claim 1 wherein the non-mammalian transgenic organism comprises a transgene designed to produce Parkinson's disease in the organism.

8. The method of claim 1 wherein the performing the plurality of the other tests further comprises determining antioxidant capabilities for the at least one of the CR mimetic or the CR mimetic candidate and determining antioxidant capabilities comprises determining a half maximal inhibitory concentration ($IC_{50}$) of the CR mimetic or the CR mimetic candidate having a dose dependent scavenging effect on a hydroxyl radical is consistent with a scavenging effect of a known radical scavenger.

9. The method of claim 1 wherein the performing the plurality of the other tests further comprises determining antioxidant capabilities for the at least one of the CR mimetic or the CR mimetic candidate and determining antioxidant capabilities comprises determining a half maximal inhibitory concentration ($IC_{50}$) of the CR mimetic or the CR mimetic candidate having a dose dependent scavenging effect on a superoxide radical is consistent with a scavenging effect of a known superoxide radical scavenger.

10. The method of claim 1 wherein the performing the plurality of the other tests further comprises determining antioxidant capabilities for the at least one of the CR mimetic or the CR mimetic candidate and determining antioxidant capabilities comprises determining a half maximal inhibitory concentration ($IC_{50}$) of the CR mimetic or the CR mimetic candidate having a dose dependent scavenging effect on a lipid radical is consistent with a scavenging effect of a known lipid radical scavenger.

11. The method of claim 1 wherein inducing oxidative damage comprises exposing the mitochondria to acrolein or 2,2'-azobis(2-amidinopropane) dihydrochloride (AAPH).

12. The method of claim 1 wherein inducing oxidative damage comprises exposing the mitochondria to 2,2'-azobis (2-amidinopropane) dihydrochloride (AAPH) and the amount of the CR mimetic or the CR mimetic candidate sufficient to inhibit the induced oxidative damage is from 10 to 50 μg/ml.

13. The method of claim 1 wherein the non-mammalian transgenic organism comprises a human form of alpha-synuclein and the disease or ailment is Parkinson's Disease.

14. The method of claim 1 wherein the plurality of other tests comprises evaluating the effect of the CR mimetic or the CR mimetic candidate on complex I or complex II activity of the mitochondria.

15. The method of claim 1 wherein determining whether the administering improves the disease or ailment comprises:
   a climbing assay in which an onset of a loss of climbing ability of the organism is analyzed; and
   a loss of motor function of the organism is analyzed.

* * * * *